United States Patent

Dvorak et al.

[11] 4,224,224
[45] Sep. 23, 1980

[54] CERTAIN 1-(CARBOCYCLIC ARYL)-1-HALO(OR MESYLOXY OR TOSYLOXY)-2-(3'-ALKOXYCARBONYL-GUANIDINO) ETHANES

[75] Inventors: Charles A. Dvorak; Colin C. Beard, both of Palo Alto, Calif.

[73] Assignee: Syntex (U.S.A.) Inc., Palo Alto, Calif.

[21] Appl. No.: 50,836

[22] Filed: Jun. 21, 1979

Related U.S. Application Data

[62] Division of Ser. No. 840,336, Oct. 7, 1977, Pat. No. 4,172,204.

[51] Int. Cl.$^2$ .................. C07D 317/54; C07C 129/12
[52] U.S. Cl. .................. 260/340.5 R; 260/456 A; 560/24; 560/28; 560/29; 560/30
[58] Field of Search .................. 260/340.5 R, 456 A; 560/24, 28, 29, 30

[56] References Cited

U.S. PATENT DOCUMENTS 3,585,213  6/1971  Molho et al. ............... 260/340.5 R
3,896,160  7/1975  Gáetzi ........................ 560/24

Primary Examiner—Henry R. Jiles
Assistant Examiner—Bernard Dentz
Attorney, Agent, or Firm—Tom M. Moran; Gerard A. Blaufarb

[57] ABSTRACT

A method for preparing 4,5-dihydro-2-alkoxycarbonylamino-5-carbocyclic aryl imidazoles and substituted aryl derivatives thereof is disclosed. The compounds are prepared by treating a 1-(carbocyclic aryl)-2-(2',3'-bis-carboalkoxyguanidino) ethane of the formula

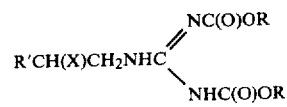

where R is $C_1$ to $C_6$ linear or branched alkyl, R' is phenyl optionally substituted with the radial methylenedioxy or at least one hydroxy, halo, trifluoromethyl, $C_1$ to $C_6$ linear or branched alkoxy, or 1-naphthyl or 2-naphthyl and X is halo, mesyloxy or tosyloxy with a protic solvent solution or dispersion of an alkali metal or alkaline earth metal hydroxide, carbonate or alkoxide. 1-(Optionally substituted carbocyclic aryl)-2-(carboalkoxyguanidino) ethanes are also disclosed herein, such prepared by treating the above bis-carboalkoxyguanadino ethane with an aprotic solvent solution or dispersion of an alkali metal or alkaline earth metal hydroxide, carbonate or alkoxide. These compounds are useful as psychotherapeutic agents in treating or palliating abnormal conditions, in mammals, which are related to the central nervous system.

13 Claims, No Drawings

CERTAIN 1-(CARBOCYCLIC ARYL)-1-HALO(OR MESYLOXY OR TOSYLOXY)-2-(3'-ALKOXYCARBONYL-GUANIDINO) ETHANES

This is a division of application Ser. No. 840,336, filed Oct. 7, 1977, now U.S. Pat. No. 172,204 issued Oct. 23, 1977.

BACKGROUND OF THE INVENTION

This invention relates to 4,5-dihydro-2-alkoxycarbonylamino-5-(carbocyclic aryl and substituted carbocyclic aryl)-imidazoles, to pharmaceutically acceptable salts thereof, and to methods for preparing such compounds. In another aspect, this invention relates to 4,5-dihydro-2-alkoxycarbonylamino-(halo-phenyl,-)imidazoles to pharmaceutically acceptable salts thereof and methods for preparing such compounds. In a further aspect, this invention relates to 4,5-dihydro-2-alkoxycarbonylamino-5-(dihalophenyl)imidazoles and the pharmaceutically acceptable salts thereof as well as methods for preparing such compounds. An additional aspect of the invention relates to 1-(carbocyclic aryl and substituted carbocyclic aryl)-2-(alkoxycarbonylguanidino) ethanes and to pharmaceutically acceptable salts thereof and methods for preparing each compound.

The invention also relates to methods for treating or palliating abnormal conditions related to the central nervous system in mammals, such as depression, anxiety, convulsions, centrally induced skeletal muscle spasms, and spasticity by the administration of the compounds of the invention.

PRIOR ART 4,5-Dihydro-2-alkoxycarbonylamino-5-(carbocyclic aryl or substituted carbocyclic aryl)imidazoles have been disclosed in copending U.S. Ser. No. 682,682 filed May 3, 1976 now abandoned, U.S. Ser. No. 708,651 filed July 26, 1976 now U.S. Pat. No. 4,088,771 and U.S. Ser. No. 803,016 filed June 3, 1977 now U.S. Pat. No. 4,110,463 and incorporated herein by reference. These compounds are primarily useful as anti-depressants. Some also display centrally acting depressant and muscle relaxant activity. Related imidazoles show antihypertensive activity, as well as exhibiting cell respiration. See for example Chaudhary, et al, J. Pharm, Sci. 65, No. 7, 1010–1014 (1976).

The processes as set forth in the above copending applications provide a variety of 5-(substituted carbocyclic aryl) imidazoles by the alkylation reaction of the corresponding β-amino-β-(carbocyclic aryl)ethylamine with 1,3-bisalkoxycarbonyl)-2-methylisothiourea. While the imidazole compounds are produced in satisfactory purity, the amine starting materials are difficult to prepare. Further, the alkylation reaction is not readily accomplished in high yields, greatly increasing the cost of the final imidazole.

SUMMARY OF THE INVENTION

It is an object of the present invention to prepare compounds represented by the following generic formula

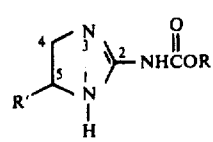

wherein
R is $C_1$ to $C_6$ linear or branched alkyl, and
R' is phenyl, optionally substituted with methylenedioxy radical or at least one halogen, trifluoromethyl, hydroxy, halo, $C_1$ to $C_6$ linear or branched alkyl or $C_1$ to $C_6$ linear or branched alkoxy or 1-naphthyl or 2-naphthyl.

It is a further object of the present invention to prepare pharmaceutically acceptable salts of the above compounds.

These and other objects of the present invention are accomplished by reacting a protic solvent-containing solution or dispersion of a 1-(carbocyclic aryl or substituted carbocyclic aryl)-2-(carboalkoxyguanidino) ethane of the formula

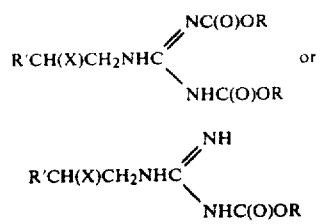

wherein R and R' are defined above and X is the radical halo, mesyloxy or tosyloxy with an alkali or alkaline earth metal hydroxide, carbonate, or alkoxide.

These and other objects of the present invention are more particularly set forth in the Description of the Preferred Embodiments.

DESCRIPTION OF THE PREFERRED EMBODIMENTS

The compounds of this invention can be represented by the following subgeneric formulas

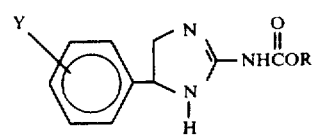

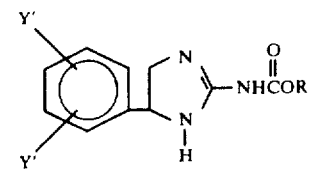

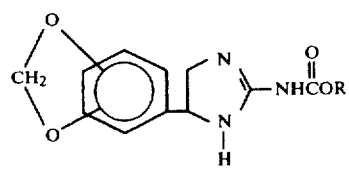

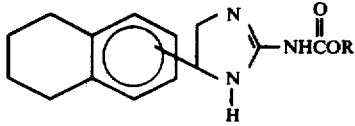

Id

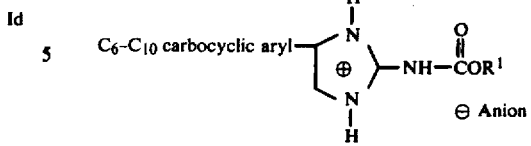

(D)

wherein

R is $C_1$ to $C_6$ linear or branched alkyl;

Y is hydrogen, hydroxy, $C_1$ to $C_6$ linear or branched alkyl, halo, trifluoromethyl, or $C_1$ to $C_6$ linear or branched alkoxy;

Y' is hydrogen, hydroxy, halo, trifluoromethyl, $C_1$ to $C_6$ linear or branched alkyl or $C_1$ to $C_6$ linear or branched alkoxy wherein the first Y' can be the same or different than the other Y';

where Y and Y' can be at any position on the carbocyclic aryl ring and the methylenedioxy group of formula (Ic) can be attached to any two adjacent carbon atoms on the carbocyclic aryl ring.

Although the compounds of the process of the invention Ia-Id will be named and described herein, for purposes of convenience, as 4,5-dihydro-2-alkoxycarbonylamino-5($C_6$ to $C_{10}$ carbocyclic aryl) imidazoles, the compounds of the invention can exist in principle in any of the ring-tautomeric forms, shown below, A, B or C, or in a protonated form as the hybrid structure D.

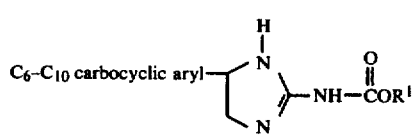
(A)

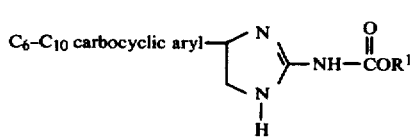
(B)

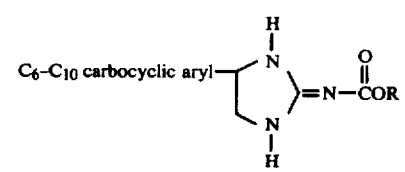
(C)

Hence, while the compounds of the invention are depicted as 4,5-dihydro-2-alkoxycarbonylamino-5-($C_6$-$C_{10}$ carbocyclic aryl) imidazoles for purposes of brevity and convenience, it should be understood that all of the above forms of the compounds are encompassed within the structural and word formula designations and are encompassed within the invention.

Preferred compounds in accordance with the process of the present invention are those where R is $C_1$ to $C_6$ linear or branched alkyl. Also preferred are compounds where Y is hydrogen, chloro, bromo or fluoro. Further, compounds where the Y''s are the same or different and are hydrogen, chloro, bromo and fluoro are preferred. Most preferred are the following compounds:

4,5-dihydro-2-methoxycarbonylamino-5-(2',6'-dichlorophenyl)imidazole, 4,5-dihydro-2-methoxycarbonylamino-5-(2'-chlorophenyl)imidazole, 4,5-dihydro-2-methoxycarbonylamino-5-(2'-bromophenyl)-imidazole, 4,5-dihydro-2-methoxycarbonylamino-5-(3'-bromophenyl)-imidazole, 4,5-dihydro-2-ethoxycarbonylamino-5-(3'-bromophenyl)-imidazole, 4,5-dihydro-2-ethoxycarbonylamino-5-(2'-chlorophenyl)-imidazole, 4,5-dihydro-2-methoxycarbonylamino-5-(2'-fluorophenyl)-imidazole, 4,5-dihydro-2-methoxycarbonylamino-5-(3'-fluorophenyl)-imidazole, 4,5-dihydro-2-methoxycarbonylamino-5-(2',6'-difluorophenyl)imidazole, and 4,5-dihydro-2-methoxycarbonylamino-5-(1-naphthyl)-imidazole.

Also included in the process of the present invention is the preparation of pharmaceutically acceptable salts of the above compounds. The preferred pharmaceutically acceptable salts are the hydrochloride, hydrobromide, nitrate, maleate and citrate salts.

The compounds prepared by the process in accordance with the present invention derive from a substituted ethanol, more particularly 1-(carbocyclic aryl or substituted carbocyclic aryl)-2-(2',3'-bis-carboalkoxyguanidino)ethanol. These compounds can be prepared by any of the well-known prior art techniques, such as illustrated, by the procedure as set forth below.

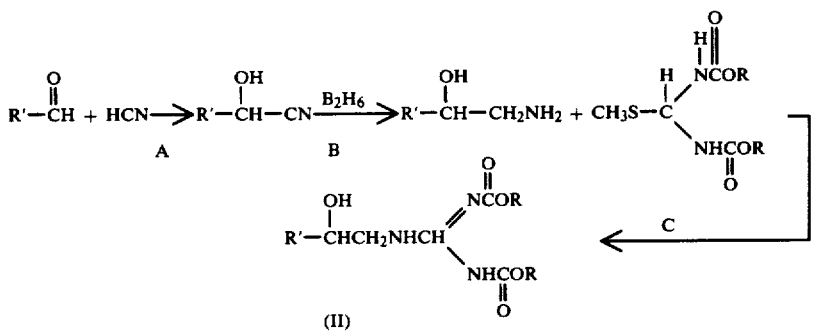

wherein R and R' are described above.

The preparation of the cyanohydrin (Sequence A) is readily achieved by the method as set forth in Cox and Stormont, Org. Synthesis, Coll. Vol. II, 7 (1941), and see Preparation 1a. The subsequent reduction of the cyanohydrin to the 1-amino-2-ethanol (Sequence B) may be accomplished by any of the classical catalytically routes. However, it has been found to be most convenient to effect such reduction with diborane as described in Long, Progr. Inorg. Chem., 15, 1-99 (1972) and see Preparation 1b. Preparative sequence C., e.g. the reaction of the amino alcohol with 1,3-bis(alkoxycarbonyl)-s-methylisothiourea is illustrated in detail in previously referenced copending application Ser. No. 682,682 filed May 3, 1976 now abandoned and Preparation 1c herein.

In the above equation, the quanidinoethanol most preferably is subjected to a mesylation reaction to yield a 1-(carbocyclic aryl)-1-mesyl-2-(2'-alkoxycarbonyl)-guanidino ethane. However, it should be understood that any other group capable of sustaining a displacement-type reaction can be used in place of the mesyloxy group on the 1-position of the ethane backbone. Other acceptable displaceable radicals are iodo, bromo, chloro, fluoro, acetoxy and the like. Preferably, the guanidinoethanol (II) may be reacted with thionyl chloride or with tosyl chloride so as to substitute the alcohol moiety with a displaceable tosyl or chloro group. See for examle Fieser & Fieser, Reagents for Organic Synthesis, page 662 (1976) and Example 2 herein.

The reaction yielding these specific guanidino ethane starting materials is illustrated as follows:

displaceable group-containing homologs the product of the reactions forming the tosylate, mesylate, chloro or other displaceable groupcontaining guanidino species is as follows:

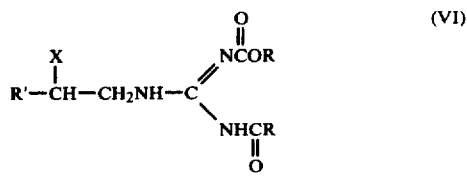

(VI)

wherein R and R' are defined above and X is any displaceable group such illustrated by mesyloxy, tosyloxy or chloro.

In the process in accordance with the present invention it is most preferred to subject the guanidinoethane substituted with a displaceable group (compound VI) to hydrolysis in a protic solvent containing solution of an alkali or alkaline earth metal hydroxide, carbonate or alkoxide. Such procedure removes the displaceable group and concertedly effects the ring closure of the guanidino ethane. The desired imidazole compounds are thereby directly formed in yields substantially greater than those experienced by the prior art techniques. The alkali metal or alkaline earth metal hydroxides, alkoxides, and carbonates useful herein are illustrated by but not limited to the compounds of potassium methoxide, potassium hydroxide, sodium hydroxide, sodium carbonate, and calcium hydroxide. The preferred protic solvents are the oxygenated hydrocarbon

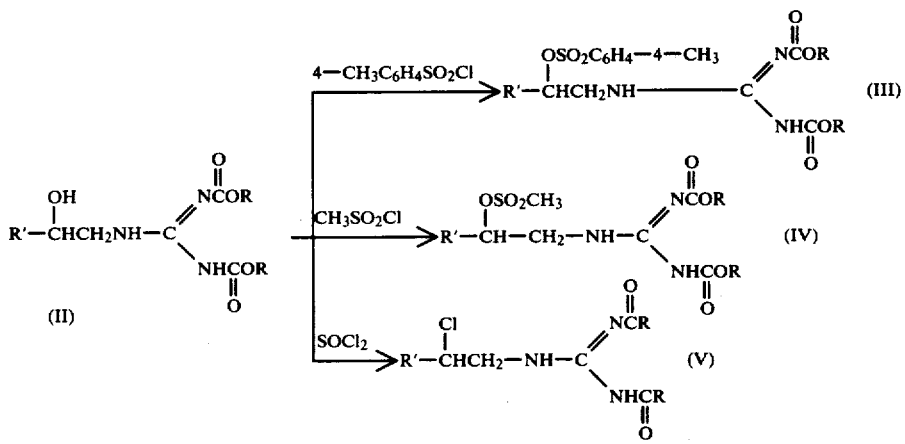

In the interest of brevity and to simplify the compounds (III), (IV), and (V) set forth above and related solvents such as methanol, ethanol, water and mixtures thereof. Compound VI and the alkali or alkaline earth metal compound dissolved or dispersed in the protic solvent are allowed to react at temperatures of from about 0° C. to about 100° C. for a period of from about ½ hour to about 14 days, using a mole ratio of the alkali or alkaline earth metal hydroxide, carbonate or alkoxide:compound (VI) of about 0.5 to 2:1. Preferably this hydrolysis/ring closure is conducted at 25°-40° C. However, temperatures, reaction times and mole ratios greater or less than the above can be used. Optimum conditions will of course vary depending on particular reactants and solvents and such can be determined by routine experimentation.

While the compound (VI) is most preferably directly converted to the imidazole of the present invention as disclosed above, it is sometimes desirable to perform the hydrolysis reaction first, isolating a chemical intermediate species. In a subsequent step this intermediate is then subjected to the ring closure reaction. In this embodiment of the present invention, the compounds (VI) are dispersed or dissolved in a suitable aprotic solvent such illustrated by pyridine, benzene, toluene, xylene and the like. By using an aprotic solvent even with the above-disclosed strong bases, the hydrolysis is effected without the ring closure. Adding the aforesaid alkali or alkaline earth metal compounds to a dispersion or solution of Compound VI in the aprotic solvent causes the hydrolysis, yielding the isolable intermediate (VII)

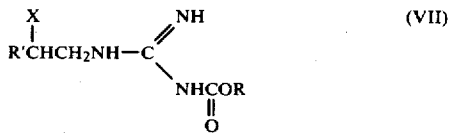

(VII)

wherein R, R' and X are defined above. Hydrolysis temperatures are typically between about 0°-100° C., preferably 20°-50° C. Preferably a dispersion or solution of a alkali or alkaline earth metal hydroxide, carbonate or alkoxide in pyridine is used to effect the hydrolysis to (VII). Ready conversion to I of Compound (VII) occurs by cyclization with the aforesaid alkali protic solvent solutions or dispersions at temperatures and times disclosed above.

The compounds preferred in accordance with this embodiment of the present invention are those bearing the substituents R, R', X, Y and Y' earlier disclosed for the compounds of Formula I. Most preferred are:

1-(2',6'-dichlorophenyl)-1-mesyl-2-(3'methoxycarbonylguanadino) ethane, 1-(2'-chlorophenyl)-1-mesyl-2-(3'methoxycarbonylguandino) ethane, 1-(2'-bromophenyl)-1-mesyl-2-(3'methoxycarbonylguanadino) ethane, 1-(3'-bromophenyl)-1-mesyl-2-(3'methoxycarbonylguanadino) ethane, 1-(3'-fluorophenyl)-1-mesyl-2-(3'methoxycarbonylguandino) ethane, 1-(2'-fluorophenyl)-1-mesyl-2-(3'methoxycarbonylguanadino) ethane, 1-(2',6'-difluorophenyl)-1-mesyl-2-(3'methoxycarbonylguandino) ethene, 1-(1'-naphthyl)-1-mesyl-2-(3'methoxycarbonylguandino) ethane.

Compound (VII) or their pharmaceutically acceptable salts also possess psychotherapeutic activity in treating or palliating central nervous system-related abnormal conditions in mammals.

The process of the present invention employs reactants and yields products having an asymmetric center, e.g., in the reactants, Compound (VI) and (VII), the carbon atom to which R' is attached and in Compound (I), the imidazole ring carbon atom to which R' is attached. These compounds exist as optically active isomers and, as such, the illustrative formulas herein are intended to represent (+) and (−) optical isomers as well as mixtures thereof. Accordingly, the individual isomers as well as racemic mixtures of these isomers are encompasssed within the process of the present invention. Resolution of the respective optical isomers can be carried out by prior art resolution procedures such as described in *Ann. Chem.*, Col. 595, page 143 (1932).

A further understanding of the invention can be had from the following non-limiting preparations and examples; wherein unless expressly stated to the contrary, racemates are used as starting material and corresponding racemic mixtures are obtained as products.

PREPARATION 1

General procedure for the preparation of the 1-(carbocyclic aryl)-2-aminoethanol intermediates as specifically illustrated by the synthesis of 1-(2,6-dichlorophenyl)-2-aminoethanol.

(a) A solution of 750 g. of benzaldehyde in 1.5 liters of dimethylsulfoxide was cooled to 0° C. and 590 g. of glacial acetic acid added. To the resulting solution was added over a 60 minute period a solution of 420 grams of sodium cyanide in 600 ml of deionized water. The solution was cooled to 5°-15° C. during the addition. The mixture was stirred for an additional 60 minutes at 15° C. Thin layer chromatography indicated complete reaction. The reaction solution was added to 14 liters of deionized water and then extracted with 5 liters of ether. The ether phase was separated and the solution diluted with a mixture of 2.5 liters ether and 3.8 liters hexane. After washing with water (three times—6 liters total), the ether layer was filtered through anhydrous sodium sulfate and stored overnight over anhydrous magnesium sulfate. After stirring for 30 minutes, filtering and washing the filter cake with 1 liter ether, the filtrate was evaporated to dryness yielding 2,6-dichlorophenylcyanohydrin.

(b) To a solution of the 2,6-dichlorophenylcyanohydrin from (a) in 3.75 liters of tetrahydrofurane was added 4.88 liters of a 1N solution of diborane in tetrahydrofurane. The diborane was added under nitrogen over a period of about 75 minutes with cooling, maintaining a reaction solution temperature of 28°-32° C. The solution was stirred for an additional 60 minutes. Thin layer chromatography of the resulting solution indicated complete reaction had occurred. The solution was cooled to 0° C. and 300 ml of deionized water added over 10 minutes. The resulting mixture was evaporated to dryness and 3.5 liters of isopropyl alcohol added, followed by 1 liter of concentrated hydrochloric acid. After stirring overnight, the mixture was refluxed for 60 minutes and evaporated to dryness. A further 3.5 liters ofisopropyl alcohol was added, the mixture heated to reflux and evaporated to dryness to yield 1-(2,6-dichlorophenyl)-2-aminoethanol as the hydrochloride salt.

PREPARATION 2

This illustrates the method for preparing the starting material useful in the present invention, such based on a carbocyclic aryl-2-(2',3'-bis-alkoxycarbonyl)guanidino ethanol.

In this example 845 g of 1-(2',6'-dichlorophenyl)-2-aminoethanol hydrochloride (Preparation 1) was dissolved in 3.75 ml of deionized water and 405 g. of sodium bicarbonate added. The resulting mixture was stirred for 15 minutes and 3.5 l of reagent grade methanol added. A solution of 745 g of 1,3-bis-(methoxycarbonyl)-s-methylisothiourea dissolved in 3.5 l of reagent grade methanol was added to the reaction mass and the resulting mixuture heated to about 55° C. for about 1 1/4 hours. After cooling to about 20° C. and storage for 1/2 hour, the mixture was filtered and the filter cake washed with 3 l of warm (45° C. ) deionized water, followed by 1.5 l of reagent grade methanol. The solid product was dryed overnight under vacuum at 55° C., giving 1-(2',6'-dichlorophenyl)-2-(2',3'-bis-methoxycarbonyl)guanidino ethanol, 1.202 kg., m.p. 156°–157° C., (dec.). Generally, using the same procedures as set forth above but substituting other carbocyclic aryl 2-aminoethanol starting materials in place of the 1-(2',6'-dichlorophenyl)-2-aminoethanol, the following compounds are prepared:

1-(2'-chlorophenyl)-2-aminoethanol;
1-(2'-bromophenyl)-2-aminoethanol;
1-(3'-bromophenyl)-2-aminoethanol;
1-(3'-fluorophenyl)-2-aminoethanol;
1-(2'-fluorophenyl)-2-aminoethanol;
1-(2',6'-difluorophenyl)-2-aminoethanol; and
1-(1-naphthyl)-2-aminoethanol.

EXAMPLE 1

The process for the preparation of 4,5-dihydro-2-alkoxycarbonylamino-4-carbocyclic aryl imidazoles in accordance with the present invention is illustrated by the following example.

To 5 l of a methylene chloride solution containing 550 g of 1-(2',6'-dichlorophenyl)-2-(2',3'-bis-methoxycarbonylguanidino) ethanol was added 530 ml of triethylamine. The mixture was stirred until a clear solution formed. Mesyl chloride, 160 ml was then added dropwise with stirring at such a rate that the solution temperature did not pass 35° C. The reaction was complete after 30 minutes. One liter of methanol was added to the reaction mass and the resulting mixture filtered. To the filtrate was added 4 l of methanol and a solution of 270 g of sodium hydroxide in 550 ml of deionized water. The mixture was vigorously agitated and heated to about 40° C. for one hour. The reaction solution was then vacuum distilled until approximately 5 l of distillate had been collected. After addition of 8 l of deionized water to the distillation flask, vacuum distillation was continued, collecting 3 l of distillate. The pot residue was cooled to about 20° C. and stirred for about 1 hour. The imidazole product precipitated from the residual reaction solution and was filtered, washed with 3 l of deionized water then 1 liter of methanol. Drying at 65° C. in a vacuum oven gave 403 g of 4,5-dihydro-2-methoxycarbonylamino-5-(2',6'-dichlorophenyl)imidazole, m.p. 231°–232° C. (dec.).

Using a procedure identical to that set forth in the above Example 1, but using the compounds listed in Preparation 2:

4,5-dihydro-2-methoxycarbonylamino-5-(2'-chlorophenyl)-imidazole;
4,5-dihydro-2-methoxycarbonylamino-5-(2'-bromophenyl)-imidazole;
4,5-dihydro-2-methoxycarbonylamino-5-(3'-bromophenyl)-imidazole;
4,5-dihydro-2-methoxycarbonylamino-5-(3'-fluorophenyl)-imidazole;
4,5-dihydro-2-methoxycarbonylamino-5-(2',6'-difluorophenyl)imidazole; and
4,5-dihydro-2-methoxycarbonylamino-5-(1-naphthyl)imidazole.

EXAMPLE 2

The process of the present invention is further illustrated by the preparative route as set forth in this example.

To 1 gram of 1-(2',6'-dichlorophenyl)-2-(2',3'-bismethoxycarbonylguanidino) ethanol dissolved in 20 ml of methylene chloride was added dropwise with cooling at 0° C. 0.35 g of thionyl chloride. At the conclusion of the addition period, the solution was stirred for an additional 60 minutes at room temperature. After the addition of 20 ml of methyl alcohol, a solution of 0.5 g of sodium hydroxide in 2 ml of water was added and the resulting mixture refluxed for 60 minutes. The reaction solution was evaporated to low volume under vacuum and 50 ml of water added. The precipitated solid was collected, washed with methanol, followed by water and dried. 4,5-Dihydro-2-methoxycarbonylamino-5-(2',6'-dichlorophenyl)imidazole was isolated, 0.3 g, m.p. 229–230 (dec.).

EXAMPLE 3

The following example is illustrative of a further embodiment of the present invention wherein the hydrolysis of displaceable group-substituted guanidino ethane is carried out in an aprotic solvent.

(a) To 10 ml of a methylene chloride solution containing 1.0 g 1-(2',6'-dichlorophenyl)-2-(2',3'-biscarbomethoxycarbonylguanidino)ethanol was added to 1.3 ml triethylamine. The mixture was stirred and 0.29 ml mesylchloride was added dropwise. The reaction solution was cooled during this addition so that the temperature did not rise above 35° C. After 1/2 hr. the reaction mixture was filtered and the filtrate was evaporated to dryness. The residue was stirred with 10 ml tetrahydrofuran. The mixture was filtered and the filtrate was evaporated to dryness. Trituration of the residue with isopropanol afforded 0.65 g of pure 1-(2',6'dichlorophenyl)-1-mesyl-2-(2',3'-bismethoxycarbonylguanidino) ethane, m.p. 109°–110°(dec).

(b) The above guanidino ethanol 0.4 g was dissolved in 6 ml of pyridine and 0.1 g of sodium hydroxide dissolved in 0.5 ml of water was added. The solution was allowed to stand overnight at 25° C. The addition of 30 ml of water caused a crystalline solid to precipitate. The solid was filtered, washed with water and dried giving 0.25 g of 1-mesyl-1-(2',6'-dichlorophenyl)-2-(3'-methoxycarbonyl)guanidino ethane, m.p. 194°–195° C. (dec.).

By the same technique as above, but using other 1-(carbocyclic aryl)-2-(2',3'-bis-methoxycarbonyl)-guanidino ethanol, the following are prepared:

1-mesyl-1-(2'-chlorophenyl)-2-(3'-methoxycarbonyl)-guanidino ethane;
1-mesy-1-(2'-bromophenyl)-2-(3'-methoxycarbonyl)-guanidino ethane;

1-mesy-1-(3'-bromophenyl)-2-(3'-methoxycarbonyl)-guanidino ethane;

1-mesy-1-(3'-fluorophenyl)-2-(3'-methoxycarbonyl)-guanidino ethane;

1-mesy-1-(2'-fluorophenyl)-2-(3'-methoxycarbonyl)-guanidino ethane;

1-mesyl-1-(2',6'difluorophenyl)-2-(3'-methoxycarbonyl)-guanidino ethane; and 1-mesy-1-(1-naphthyl)-2-(3'-methoxycarbonyl)-guanidino ethane.

EXAMPLE 4

This example illustrates the cyclization of the monoalkoxy guanidino compounds illustrated in Example 3.

The mono methoxy carbonyl guanidino ethane prepared as illustrated in Example 3 was dissolved in methylene chloride (0.25 g in 2.5 ml of solvent). A solution of 0.15 g sodium hydroxide in 2.5 ml methanol/water was added and the mixture vigorously agitated with heating to 40° C. for 60 minutes. The reaction mixture was evaporated to dryness and the residue washed with water then methanol. The product was identified as 4,5-dihydro-2-methoxycarbonylamino-5-2',6'-dichlorophenyl)imidazole, m.p. 231°-232° C. (dec).

Similarly prepared by this technique are:

4,5-dihydro-2-methoxycarbonylamino-5-(2'-chlorophenyl)-imidazole;

4,5-dihydro-2-methoxycarbonylamino-5-(2'-bromophenyl)-imidazole;

4,5-dihydro-2-methoxycarbonylamino-5-(3'-bromophenyl)-imidazole;

4,5-dihydro-2-methoxycarbonylamino-5-(3'-fluorophenyl)-imidazole;

4,5-dihydro-2-methoxycarbonylamino-5-(2',6'-difluorophenyl)imidazole; and 4,5-dihydro-2-methoxycarbonylamino-5-(1-naphthyl)-imidazole.

What is claimed is:

1. A compound of the formula $$R'-\overset{X}{\underset{|}{CH}}-CH_2NH-C\overset{NH}{\underset{NHCOR}{\diagdown}}$$
$$\phantom{R'-CH-CH_2NH-C\diagdown}\overset{\|}{O}$$

wherein

R is $C_1$ to $C_6$ linear or branched alkyl,

R' is phenyl, optionally substituted with the radical methylenedioxy or with at least one hydroxy, trifluoromethyl, halo, $C_1$ to $C_6$ linear or branched alkoxy or $C_1$ to $C_6$ linear or branched alkyl, or 1-naphthyl or 2-naphthyl and X is the radical selected from the group halo, mesyloxy, and tosyloxy and pharmaceutically acceptable salts thereof.

2. The compound of claim 1 having the formula $$Y'\!-\!\!\bigcirc\!\!-\!\!\overset{X}{\underset{|}{CHCH_2NH}}\!-\!C\overset{NH}{\underset{NHCOR}{\diagdown}}$$

where R is defined above and Y' is hydrogen, hydroxy, trifluoromethyl, fluoro, chloro, bromo, $C_1$ to $C_6$ linear or branched alkyl or $C_1$ to $C_6$ linear or branched alkoxy, wherein the first Y' is the same or different than the other Y'.

3. The compound of claim 2 wherein R is $C_1$ to $C_4$ linear or branched alkyl and Y"s are the same or different and are hydrogen, chloro, bromo or fluoro.

4. The compound of claim 3 wherein R is methyl or ethyl and the Y"s are the same.

5. The compound of claim 1 having the formula $$\overset{CH_2}{\underset{CH_2}{\overset{\diagup}{O}\diagdown}}\!\bigcirc\!\!-\!\!\overset{X}{\underset{|}{CHCH_2NH}}\!-\!C\overset{NH}{\underset{NHCOR}{\diagdown}}$$

6. The compound of claim 5 wherein R is $C_1$ to $C_4$ linear or branched alkyl.

7. The compound of claim 6 wherein R is methyl or ethyl.

8. The compound of claim 1 having the formula $$Y\!-\!\!\bigcirc\!\!-\!\!\overset{X}{\underset{|}{CH}}\!-\!CH_2NH\!-\!C\overset{NH}{\underset{NHCOR}{\diagdown}}$$

wherein Y is hydrogen, hydroxy, halo, trifluoromethyl, $C_1$ to $C_6$ linear or branched alkyl, or $C_1$ to $C_6$ linear or branched alkoxy.

9. The compound of claim 8 wherein R is $C_1$ to $C_4$ linear or branched alkyl and Y is hydrogen, chloro, bromo or fluoro.

10. The compound of claim 9 wherein R is methyl or ethyl and Y is chloro, bromo or fluoro.

11. The compound of claim 1 having the formula $$\bigcirc\!\!\bigcirc\!\!-\!\!\overset{X}{\underset{|}{CH}}\!-\!CH_2NH\!-\!C\overset{NH}{\underset{NHCOR}{\diagdown}}$$

12. The compound of claim 11 wherein R is $C_1$ to $C_4$ linear or branched alkyl.

13. The compound of claim 12 that is 1-mesyl-1-(1-naphthyl)-2-(3'-methoxycarbonyl) guanidino ethane.

* * * * *